US005726145A

United States Patent [19]

Julemont et al.

[11] Patent Number: 5,726,145

[45] Date of Patent: Mar. 10, 1998

[54] COLOR PERFUME CONCENTRATES

[75] Inventors: Jean Julemont, Verviers; Marianne Mahieu, Ferrieres, both of Belgium

[73] Assignee: Colgate-Palmolive Company, Piscataway, N.J.

[21] Appl. No.: 703,221

[22] Filed: Aug. 26, 1996

[51] Int. Cl.$^6$ .......... A61K 7/46

[52] U.S. Cl. .......... 512/1; 512/2; 252/122

[58] Field of Search .......... 512/1, 2; 252/122

[56] References Cited

U.S. PATENT DOCUMENTS

| | | | |
|---|---|---|---|
| Re. 35,407 | 12/1996 | Weisenfeldt et al. | 526/256 |
| 3,992,332 | 11/1976 | Zenon | 252/548 |
| 4,128,508 | 12/1978 | Munden | 512/1 |
| 4,289,644 | 9/1981 | Steinhauer et al. | 252/127 |
| 5,076,954 | 12/1991 | Loth et al. | 252/122 |
| 5,082,584 | 1/1992 | Loth et al. | 252/122 |
| 5,108,643 | 4/1992 | Loth et al. | 252/174.11 |
| 5,389,607 | 2/1995 | Dartnell et al. | 512/3 |
| 5,393,454 | 2/1995 | Mondin et al. | 252/174.23 |
| 5,393,468 | 2/1995 | Erilli et al. | 252/550 |

*Primary Examiner*—James H. Reamer
*Attorney, Agent, or Firm*—Richard E. Nanfeldt; James M. Serafino

[57] ABSTRACT

A liquid color/perfume concentrate comprising approximately by weight: 0.01% to 85% of a polymer bound water soluble azo dye and 99.95% to 15% of a perfume.

4 Claims, No Drawings

COLOR PERFUME CONCENTRATES

FIELD OF THE INVENTION

The present invention relates to a liquid color/perfume concentrate containing a colorant and a perfume with a liquid cleaning composition.

BACKGROUND OF THE INVENTION

Over the last thirty years, all purpose cleaners have been continuously improved to increase both efficacy and consumer convenience. This way, they moved from powder form to liquid form, then from traditional emulsions to eventually microemulsions. Significant progress was also achieved in tailoring the surfactants, reducing builders, allowing superior cleaning performance without the drawback of residues, too much foaming or harshness to both surfaces and skin.

These progresses resulted in offering to consumer more satisfaction in their cleaning task. In parallel to that, the "perfuming" function, initially inexistant, was progressively developed, first to cover the base odor, then to further deliver a nice pleasant odor during and after cleaning. The "perfume" attribute therefore became more and more important to consumers aside the "performance" attributes. A logical result of this trend is that an increased number of perfume variants are offered in the market place to satisfy consumers choice. Indeed, one can observe that the more perfume variants offered, the higher market shares. The drawback of this approach of more perfume variants for the same APC (all purpose cleaning) brand is an increased cost through an increased number of SKU's, an important reference cost when introducing a new variant, as well as additional production/warehousing costs.

An approach to offer a large range of perfume variants, while even decreasing the number of references, would be to propose the principle of "consumer postdifferentiation", i.e. selling on one hand the base formula—perfume and color free—and on the other hand, perfume dose to be postadded to the base formula at consumer stage.

This approach has never been proposed for APC products, as a real commercial product in the APC business. The potential reason is that in an APC product, two main difficulties have to be solved to ensure an easy consumer "postdifferentiation". Indeed, in most of the cases, traditional APC emulsions do not allow postaddition of perfume without either bringing minimum energy to the system to incorporate perfume in the base product, or at least adding a significant amount of perfume solubilizers in the base product; furthermore, in the case of "perfume dose" approach, the "perfume dose" should preferably contain both perfume AND DYE to "identify" each perfume variants. Unfortunately, most of the dyes commonly used to color APC products are hydrosoluble and therefore incompatible with perfume.

The objective of this invention is to make and/or commercialize APC multiperfume variants through the combination of "colored perfume doses" to be postadded to APC base product as well as the relevant process/formula to obtain easy to make "final" product.

SUMMARY OF THE INVENTION

The present invention relates to color/perfume concentrates containing a perfume which can be added to a liquid cleaning composition such as a light duty liquid cleaning composition,, a microemulsion cleaning composition, an all purpose cleaning composition, a fabric care composition, a body care composition, a body cleaning composition or a shampoo composition.

The color/perfume concentrate comprises by weight:

(a) 0.01% to 85%, more preferably 0.01% to 50% of at least one polymeric dye such as Liquitint® manufactured by Milliken;

(b) 15% to 99.99% g more preferably 50% to 99.99% of a perfume; and (c) 0 to 99% a nonionic surfactant or an ethoxylated glycerol type compound.

The cleaning composition can be mixed with the color/perfume concentrate in any desired weight ratio, preferably about 0.01 to 90, more preferably about 0.5 to about 5. This permits the end user to design a liquid cleaning composition that has a particular color and a particular smell that is pleasing to his senses.

The present invention also relates to a process which comprises the step of mixing the color/perfume concentrate with the liquid cleaning composition. For example, the color/perfume concentrate can be packaged in preselected unit dosages which can be added to the liquid cleaning composition contained in a separate package. After the addition of the color/perfume concentrate to the cleaning composition, the user shakes the liquid cleaning composition containing the color/perfume concentrate until uniform mixing has been achieved.

DETAILED DESCRIPTION OF THE INVENTION

The present invention relates to color/perfume concentrate compositions which comprise by weight:

(a) 0.01% to 85%, more preferably 0.01% to 50% of at least one polymeric dye such as Liquitint® manufactured by Milliken;

(b) 15% to 99.99%, more preferably 50% to 99.99% of a perfume; and (c) 0 to 99.99% a nonionic surfactant or an ethoxylated glycerol type compound.

The color/perfume concentrates containing a perfume which can be added to a liquid cleaning composition such as a light duty liquid cleaning composition, a microemulsion cleaning composition, an all purpose cleaning composition, a fabric care composition, a body care composition, a body cleaning composition or a shampoo composition.

The polymeric dye employed in the instant color/perfume concentrate compositions are water soluble and oil miscible. These dyes are polymer bound azo dye colorant which are nonionic in character manufactured by Milliken Chemical under the branch name of Liquitint®. The available liquid dyes are lemon yellow, reddish tint yellow, amber color, bright blue, reddish blue, royal blue, violet, orange, bluish red, medium red, bright pink, grass green, blue-green, and medium green. Obviously, more than one liquitint dye can be added to the instant color concentrate to form other colors than those previously identified.

The term "perfume" which is used in the color/perfume concentrate is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, ketones, aromatic compounds and varying amounts of essential oils (e.g., terpenes)

such as from 0% to 80%, usually from 10% to 70% by weight. The essential oils themselves are volatile odoriferous compounds and also serve to dissolve the other components of the perfume.

The nonionic surfactant which is used in the color/perfume concentrates can also be optionally contained in the cleaning composition.

The water soluble nonionic surfactants utilized in the color/perfume concentrates are commercially well known and include the primary aliphatic alcohol ethoxylates and secondary aliphatic alcohol ethoxylates. The nonionic synthetic organic surfactants generally are the condensation products of an organic aliphatic hydrophobic compound and hydrophilic ethylene oxide groups. Any hydrophobic compound having a hydroxy group can be condensed with ethylene oxide or with the polyhydration product thereof, polyethylene glycol, to form a water soluble nonionic surfactant.

The nonionic surfactant class includes the condensation products of a higher alcohol (e.g., an alkanol containing about 8 to about 18, more preferably about 8 to about 12, carbon atoms in a straight or branched chain configuration) condensed with about 10 to 20 moles of ethylene oxide, for example, decyl, lauryl or myristyl alcohol condensed with about 12 moles of ethylene oxide (EO), myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 10 moles of EO per mole of total alcohol or about 10 moles of EO per mole of alcohol.

A preferred group of the foregoing nonionic surfactants are the Neodol ethoxylates (Shell Co.), which are higher aliphatic, primary alcohol containing about 8 to 15 carbon atoms, such as $C_9$–$C_{11}$ alkanol condensed with 8 moles of ethylene oxide (Neodol 91-8), $C_{9-11}$ alkanol condensed with 12 moles ethylene oxide (Neodol 91-12).

Most preferred nonionic surfactants present will be condensation products of a fatty alcohol of 8 to 20 carbon atoms with from 3 to 20 moles of ethylene oxide, preferably of a linear alcohol of 9 to 15 carbon atoms, such as 9–11 or 11–13 carbon atoms, or averaging about 10 or 12 carbon atoms, with 3 to 15 moles of ethylene oxide, such as 3–7 or 5–9 moles of ethylene oxide, e.g., about 5 or 7 moles thereof. In place of the higher fatty alcohol one may use an alkylphenol, such as one of 8 to 10 carbon atoms in a linear alkyl, e.g., nonylphenol, and the phenol may be condensed with from 3 to 20 ethylene oxide groups, preferably 8 to 15. Similarly functioning nonionic surfactants that are polymers of mixed ethylene oxide and propylene oxide may be substituted, at least in part, for the other nonionics. Among such are those sold under the trademarks Synperonic and Plurafac, such as Synperonic RA-30 and Plurafac LF-400, which are available from ICI and BASF, respectively. Preferred such nonionics contain 3 to 12 ethoxides, more preferably about 7, and 2 to 7 propoxy groups, more preferably about 4, and such are condensed with a higher fatty alcohol of 12–16, more preferably 13–15 carbon atoms, to make a mole of nonionic surfactant.

The light duty liquid compositions to which the color/perfume concentrate can be added comprise approximately by weight:

(a) 5% to 45% of at least one surfactant selected from the group consisting of sulfate anionic surfactant, sulfonate anionic surfactant, mixtures of esterified, partially esterified and nonesterified polyhydric alcohols, carboxylate anionic surfactant, nonionic surfactants and zwitterionic surfactants and mixtures thereof;

(b) 0–20% of a solubilizer; and (c) the balance being water.

An all purpose cleaning composition to which the color/perfume concentrate can be added comprises approximately by weight:

(a) 5% to 45% of at least one surfactant selected from the group consisting of sulfate anionic surfactant, sulfonate anionic surfactant, mixtures of esterified, partially esterified and nonesterified polyhydric alcohols, carboxylate anionic surfactant, nonionic surfactants and zwitterionic surfactants and mixtures thereof;

(b) 0 to 15% of a cosurfactant; and (c) the balance being water.

The microemulsion composition to which the color/perfume concentrate can be added comprises approximately by weight:

(a) 5% to 45% of at least one surfactant selected from the group consisting of sulfate anionic surfactant, sulfonate anionic surfactant, mixtures of esterified, partially esterified and nonesterified polyhydric alcohols, carboxylate anionic surfactant, nonionic surfactants and zwitterionic surfactants and mixtures thereof;

(b) 1% to 15% of a cosurfactant; and (c) the balance being water.

The shampoo composition to which the color/perfume concentrate can be added comprises approximately by weight:

(a) 10% to 30% of an ammonium or alkali metal salt of an ethoxylated $C_8$–$C_{16}$ alkyl ether sulfate, a $C_8$–$C_{16}$ alkyl benzene sulfonate or a $C_8$–$C_{16}$ alkyl sulfate;

(b) 0.1% to 4% of a alkyl polysiloxane;

(c) 0to 3% of a $C_{12-16}$ alkyl alkanol amide;

(d) 0.1% to 3% of a $C_{20}$–$C_{40}$ alcohol;

(e) 0 to 1.5% of a distearyldimonium chloride;

(f) 0 to 4% of a zwitterionic sulfonate; and (g) the balance being water.

The body cleaning composition to which the color/perfume concentrate can be added comprises approximately by weight:

(a) 6% to 30% of an ethoxylated $C_8$–$C_{16}$ alkyl ether sulfate;

(b) 2% to 16% of a $C_8$–$C_{16}$ alkyl sulfate or a $C_8$–$C_{16}$ alkyl benzene sulfonate;

(c) 1% to 8% of a zwitterionic surfactant;

(d) 1% to 8% of a $C_{12-16}$ alkyl alkanol amide; and (e) the balance being water.

The fabric care cleaning composition to which the color/perfume concentrate can be added comprises approximately by weight:

(a) 5% to 40% of a sulfate or sulfonate surfactant;

(b) 0.05% to 5% of at least one enzyme; and (c) the balance being water.

Suitable water-soluble non-soap, anionic surfactants used in the instant cleaning compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, or magnesium, with the sodium and magnesium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH{=}CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735, 096.

Examples of satisfactory anionic sulfate surfactants are the $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_n\,OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the alkyl ether polyethenoxy sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of $CH_2$, $(C(O)R_1$ and

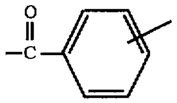

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

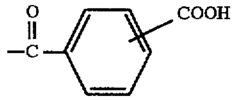

and $C_{10}$–$C_{12}$ alkyl ether polyethenoxy (5–7) $CH_2COOH$. These compounds may be prepared by considering ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

The zwitterionic surfactant used in forming the cleaning composition is a water soluble betaine having the general formula:

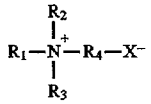

wherein $X^-$ is selected from the group consisting of $COO^-$ and $SO_3^-$ and $R_1$ is an alkyl group having 10 to about 20 carbon atoms, preferably 12 to 16 carbon atoms, or the amido radical:

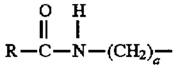

wherein R is an alkyl group having about 9 to 19 carbon atoms and a is the integer 1 to 4:$R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Three preferred betaine surfactants are Genagen CAB and Rewoteric AMB 13 and Golmschmidt Betaine L7.

The instant cleaning composition can contains a composition (herein after referred to as ethoxylated glycerol type compound) which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is a mixture of Formula (I)

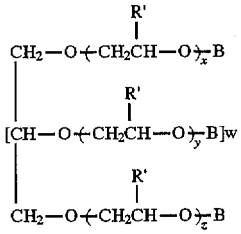

and

Formula (II)

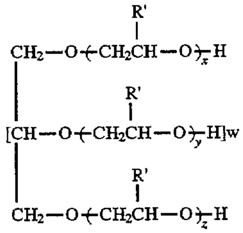

wherein w equals one to four, most preferably one. B is selected from the group consisting of hydrogen or a group represented by:

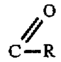

wherein R is selected from the group consisting of alkyl group having about 6 to 22 carbon atoms, more preferably about 11 to about 15 carbon atoms and alkenyl groups having about 6 to 22 carbon atoms, more preferably about 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals about 2 to about 100, preferably 4 to about 24 and most preferably about 4 to 19, wherein in Formula (I) the ratio of monoester/diester/triester is 45 to 90/5 to 40/1 to 20, more preferably 50 to 90/9 to 32/1 to 12, wherein the ratio of Formula (I) to Formula (II) is a value between about 3 to about 0.02, preferably 3 to about 0.1, most preferably about 1.5 to about 0.2, wherein it is most preferred that there is more of Formula (II) than Formula (I) in the mixture that forms the compound.

The ethoxylated glycerol type compound used in the cleaning composition is manufactured by the KAO Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than about 1.7, more preferably less than about 1.5 and most preferably less than about 1.0. The ethoxylated glycerol type compound has a molecular weight of about 400 to about 1600, and a pH (50 grams/liter of water) of about 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of about 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition >100 mg/liter; acute toxicity for Daphniae >100 mg/liter and acute fish toxicity >100 mg/liter. The Levenol compounds have a ready biodegradability higher than 60% which is the minimum required value according to OECD 301B measurement to be acceptably biodegradable.

Polyesterified nonionic compounds also useful in the cleaning compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is preferred is a polyoxyethylene (45) Palm Kernel Glyceride have 45 EO groups.

The surfactants in the light duty liquid, shampoo or body cleaning composition can be solubilized in one preferred embodiment of the invention in an aqueous medium comprising water and a mixture of an alkyl monoalkanol amides such as $C_{12}$–$C_{14}$ alkyl monoethanol amide (LMMEA) at a concentration of 1 to 4 wt. %, and an alkyl diethanol amides such as coco diethanol amide (CDEA) or lauryl diethanol amide (LDEA) at a concentration of 1 to 4 wt. % wherein the ratio of monoethanol amide to diethanol amide is about 3:1 to about 1:3. The instant formulas may contain both alkyl monoethanol amide and alkyl diethanol amide.

Other solubilizing agents are $C_2$–$C_3$ mono and di-hydroxy alkanols, e.g., ethanol, isopropanol and propylene glycol. Suitable water soluble hydrotropic salts include sodium, potassium, ammonium and mono-, di- and triethanolammonium salts. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from about 1% to 15%, preferably 2% to 12%, most preferably 3%–8%, by weight of the detergent composition with the proportion of ethanol, when present, being 5% of weight or less in order to provide a composition having a flash point above about 46° C. Preferably the solubilizing ingredient will be a mixture of ethanol and a water soluble salt of a $C_1$–$C_3$ substituted benzene sulfonate hydrotrope such as sodium xylene sulfonate or sodium cumene sulfonate or a mixture of said sulfonates or ethanol and urea. Inorganic alkali metal or alkaline earth metal salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution.

A cosurfactant can be used in forming the all purpose hard surface or microemulsion cleaning compositions of the instant invention. Suitable cosurfactants over temperature ranges extending from 4° C. to 43° C. are: (1) water-soluble $C_3$–$C_4$ alkanols, polypropylene glycol of the formula $HO(CH_3CHCH_2O)_nH$ wherein n is a number from 2 to 18 and copolymers of ethylene oxide and propylene oxide and mono $C_1$–$C_6$ alkyl ethers and esters of ethylene glycol and propylene glycol having the structural formulas $R(X)_nOH$ and $R_1$ $(X)_nOH$ wherein R is $C_1$–$C_6$ alkyl, $R_1$ is $C_2$–$C_4$ acyl group, X is $(OCH_2CH_2)$ or $(OCH_2(CH_3)CH)$ and n is a number from 1 to 4.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. Representative members of the aliphatic carboxylic acids include $C_3$–$C_6$ alkyl and alkenyl monobasic acids such as acrylic acid and propionic acid and dibasic acids such as glutaric acid and mixtures of glutaric acid with adipic acid and succinic acid, as well as mixtures of the foregoing acids.

While all of the aforementioned glycol ether compounds and acid compounds provide the described stability, the most preferred cosurfactant compounds of each type, on the basis of cost and cosmetic appearance (particularly odor), are diethylene glycol monobutyl ether and a mixture of adipic, glutaric and succinic acids, respectively. The ratio of acids in the foregoing mixture is not particularly critical and can be modified to provide the desired odor. Generally, to maximize water solubility of the acid mixture glutaric acid, the most water-soluble of these three saturated aliphatic dibasic acids, will be used as the major component.

Still other classes of cosurfactant compounds providing stable microemulsion compositions at low and elevated temperatures are the mono-, di- and triethyl esters of phosphoric acid such as triethyl phosphate.

The amount of cosurfactant which might be required to stabilize the microemulsion compositions will, of course, depend on such factors as the surface tension characteristics of the cosurfactant, the type and amounts of the analephotropic complex and perfumes, and the type and amounts of any other additional ingredients which may be present in the composition and which have an influence on the thermodynamic factors enumerated above. Generally, amounts of cosurfactant in the range of from 1 to 15 wt. %, preferably from 1.5 wt. % to 12 wt. %, provide stable microemulsions for the above-described levels of primary surfactants and perfume and any other additional ingredients.

In addition to the above-described essential ingredients required for the formation of the cleaning compositions, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level.

Thus, depending on such factors as the pH of the system, the nature of the analephotropic complex and cosurfactant, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

The cleaning compositions can optionally include from 0 to 2.5 wt. %, preferably from 0.1 wt. % to 2.0 wt. % of the composition of a $C_8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt. % of a fatty acid is used in the instant cleaning compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The cleaning composition may, if desired, also contain other components either to provide additional effect or to make the product more attractive to the consumer. The following are mentioned by way of example: Bactericides in amounts up to 1% by weight; preservatives or antioxidizing agents, such as formalin, 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the cleaning compositions exhibit stability at reduced and increased temperatures. More specifically, such compositions remain clear and stable in the range of 4° C. to 50° C., especially 10° C. to 43° C. Such compositions exhibit a pH in the acid or neutral range depending on intended end use. The liquids are readily pourable and exhibit a viscosity in the range of 6 to 60 milliPascal Second (mPas.) as measured at 25° C. with a Brookfield RVT Viscometer using a #1 spindle rotating at 20 RPM.

EXAMPLE I

A liquid composition was made by simple mixing at 25C to which color/perfume concentrates A–D were added to form microemulsion compositions E–F. The liquid composition was: sodium paraffin sulfonate surfactant, Levenol F-200, Diethylene glycol monobutyl ether, Water

| | A | B | C | D |
|---|---|---|---|---|
| Floral perfume | 99.75 | | | |
| Lemon perfume | | 98.75 | | |
| Exotic perfume | | | 98.625 | |
| Lavanda perfume | | | | 99.75 |
| Liquitint patent blue 710230 | 0.25 | | | |
| Liquitint yellow EC710406 | | 1.25 | 1.25 | |
| Liquitint blue 710407 | | | 0.125 | |
| Liquitint violet PG710233 | | | | 0.125 |
| Liquitint red RL710208 | | | | 0.125 |

The letdown ratio of:

Liquid composition to color perfume concentrate to obtain 0.8 wt. % of the perfume in the final composition was

| | A | B | C | D |
|---|---|---|---|---|
| Liquid composition | 125:1 | 123:1 | 123:1 | 125:1 |

What is claimed is:

1. A liquid color/perfume concentrate comprising approximately by weight;

(a) 0.01% to 50% of a polymer bound water soluble nonionic azo dye; and (b) 50% to 99.99% of a non-water soluble perfume.

2. A liquid/perfume concentrate further including a nonionic surfactant or ethoxylated glycerol type compound.

3. A process for adding fragrance and color to a liquid composition which comprises the step of adding a liquid color/perfume concentrate comprising approximately by weight 50% to 99.99% of a perfume and 0.01% to 50% of a polymer bound water soluble nonionic azo dye to a liquid composition.

4. A process according to claim 3, wherein said liquid composition is selected from the group consisting of light duty liquid compositions, an all purpose cleaning composition, a microemulsion composition, a shampoo composition, a body cleaning composition and a fabric care cleaning composition.

* * * * *